United States Patent [19]
Turi

[11] Patent Number: 5,556,414
[45] Date of Patent: Sep. 17, 1996

[54] COMPOSITE INTRALUMINAL GRAFT

[75] Inventor: Zoltan G. Turi, West Bloomfield, Mich.

[73] Assignee: Wayne State University, Detroit, Mich.

[21] Appl. No.: 400,902

[22] Filed: Mar. 8, 1995

[51] Int. Cl.$^6$ .................................................. A61M 29/00
[52] U.S. Cl. ................................ 606/198; 623/1; 623/12
[58] Field of Search ............................ 623/1, 11, 12; 606/108, 152–156, 191, 194, 195, 198; 604/96, 104

[56] References Cited

U.S. PATENT DOCUMENTS

| | | |
|---|---|---|
| 3,974,526 | 8/1976 | Dardik et al. ............................... 623/1 |
| 4,580,568 | 4/1986 | Gianturco . |
| 4,733,665 | 3/1988 | Palmaz . |
| 4,739,762 | 4/1988 | Palmaz . |
| 4,776,337 | 10/1988 | Palmaz . |
| 4,800,882 | 1/1989 | Gianturco . |
| 4,886,062 | 12/1989 | Wiktor . |
| 4,922,905 | 5/1990 | Strecker . |
| 4,969,458 | 11/1990 | Wiktor . |
| 5,041,126 | 8/1991 | Gianturco . |
| 5,078,735 | 1/1992 | Mobbin-Uddin ............................ 623/1 |
| 5,102,417 | 4/1992 | Palmaz . |
| 5,104,404 | 4/1992 | Wolff . |
| 5,133,732 | 7/1992 | Wiktor . |
| 5,192,297 | 3/1993 | Hull . |
| 5,195,984 | 3/1993 | Schatz . |
| 5,234,456 | 8/1993 | Silvestrini . |
| 5,258,042 | 11/1993 | Mehta . |
| 5,282,823 | 2/1994 | Schwartz . |
| 5,282,824 | 2/1994 | Gianturco . |
| 5,314,444 | 5/1994 | Gianturco . |
| 5,314,472 | 5/1994 | Fontaine . |
| 5,342,621 | 8/1994 | Eury . |
| 5,344,426 | 9/1994 | Lau et al. . |
| 5,399,352 | 3/1995 | Hanson ........................................ 623/1 |

FOREIGN PATENT DOCUMENTS 8203764  11/1982  WIPO ........................................ 623/1

OTHER PUBLICATIONS

U. Sigwart, M.D., J. Puel, M.D., V. Mirkovitch, M.D., F. Joffre, M.D., and L. Kappenberger, M.D., "Intravascular Stents to Prevent Occlusion and Restonsis After Transluminal Angioplasty", The New England Journal of Medicine, No. 12, vol. 316, 701–706, Mar. 19, 1987.

Eric J. Topol, M.D., "Textbook of Interventional Cardiology", vol. 2, Second Edition, 687–704, 712–715, 727–730, 742–745, 754–761, and 803–815, 1994.

Primary Examiner—Michael Powell Buiz
Assistant Examiner—William Lewis
Attorney, Agent, or Firm—Barnes, Kisselle, Raisch, Choate, Whittemore & Hulbert, P.C.

[57] ABSTRACT

In accordance with the present invention, a novel composite prosthesis comprises a vein and a cylindrical-shaped member. The vein is a vein segment removed from a patient and the cylindrical-shaped member, preferably an expandable stent, is glued, sutured, or in some other fashion affixed to the outside surface of the vein. The vein segment of the combination is referred to as a vein graft or vein implant to distinguish it from the vascular structure into which it is inserted as a part of the combination. This composite prosthesis is then introduced inside a body passageway, such as diseased arterial segment or inside a saphenous vein graft segment which by-passes an arterial segment. It may be introduced by placement over a balloon catheter. When the balloon is inflated the stent and vein graft expand. The stent prevents recoil and keeps the vein graft tissue in place, while the vein graft forms a new inner lining for the vessel. It is preferred that the vein graft portion of the composite prosthesis be the patient's own vein.

21 Claims, 5 Drawing Sheets

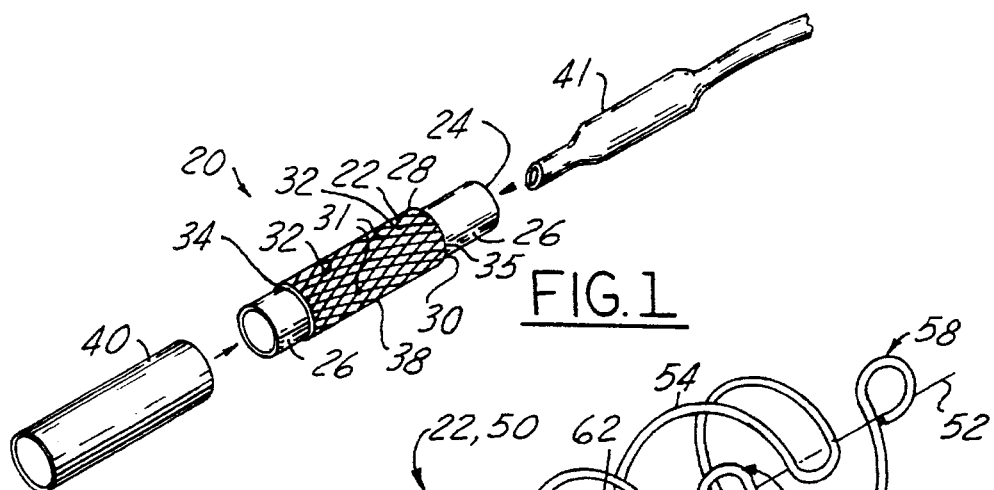
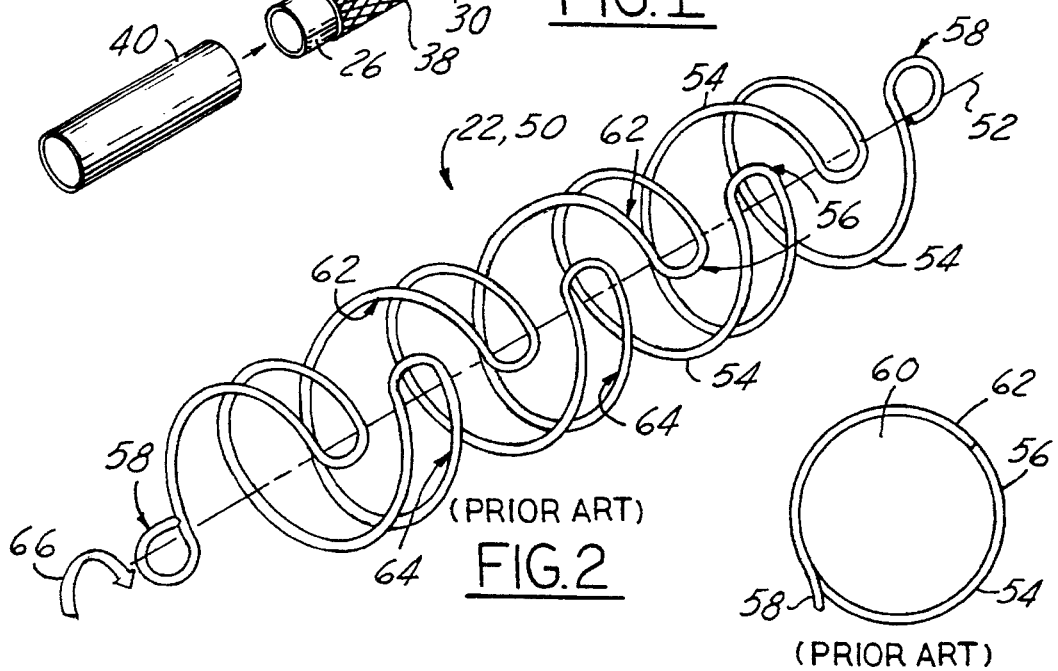
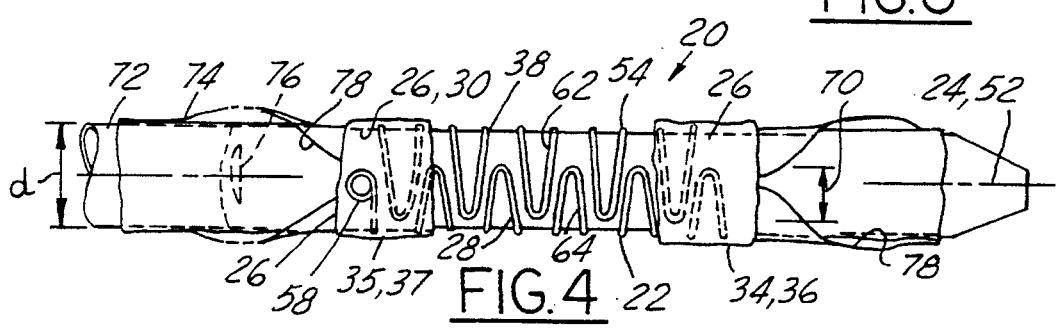

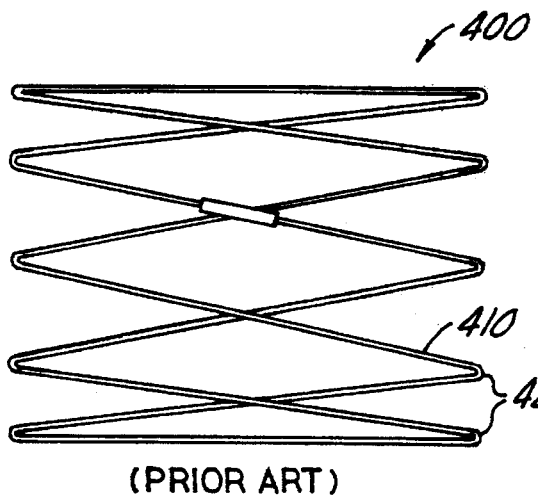
FIG. 14 (PRIOR ART)
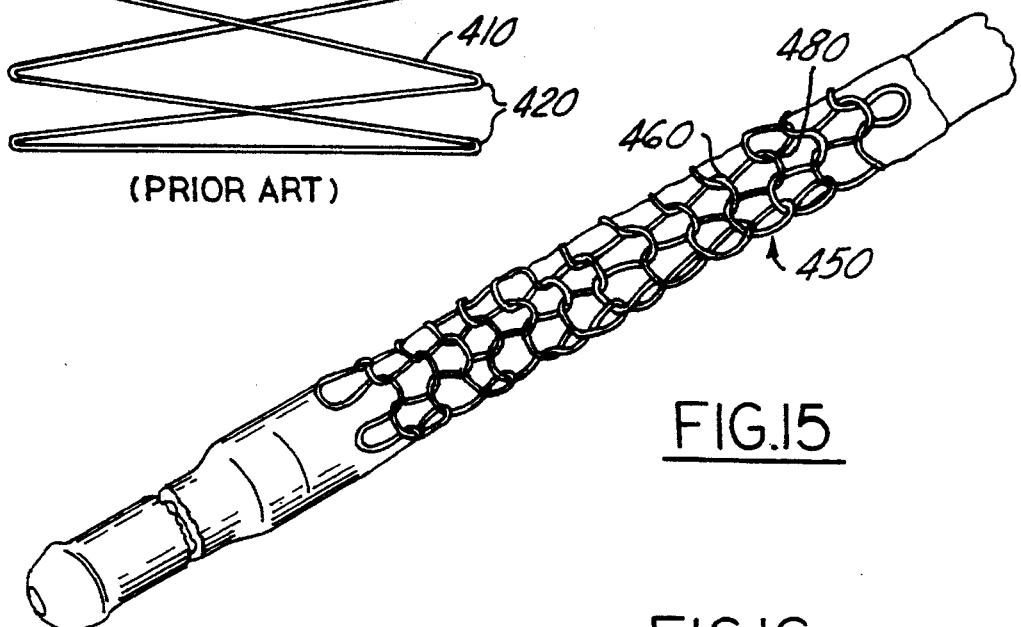
FIG. 15
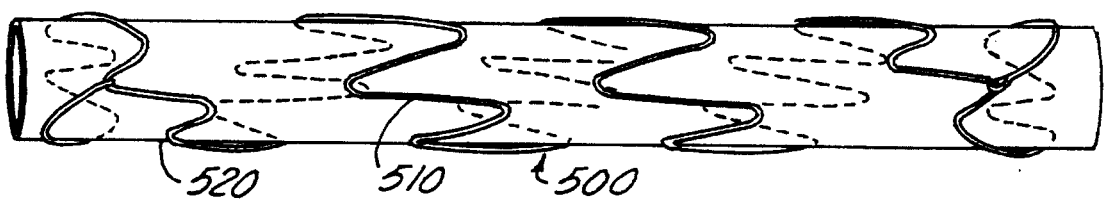
FIG. 16
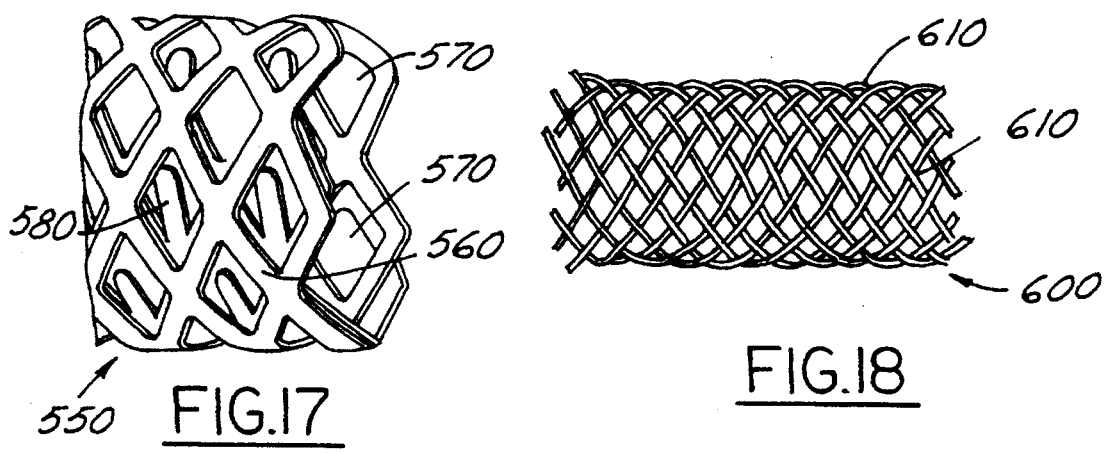
FIG. 17
FIG. 18

COMPOSITE INTRALUMINAL GRAFT

FIELD OF THE INVENTION

The invention relates to an intraluminal graft for use within a body passageway or duct and, more particularly, expandable intraluminal vascular grafts which are particularly useful for repairing blood vessels narrowed or occluded by disease; and a method and apparatus for implanting expandable intraluminal grafts.

BACKGROUND OF THE INVENTION

Stents can be used in a variety of tubular structures in the body including, but not limited to, ureters, common bile ducts, blood vessels, and the like. A stent may be used to expand a body tubular structure, maintain the lumen after expansion of the tubular structure or repair a damaged tubular segment. Stents are used, for example, after angioplasty and after atherectomy to maintain expanded lumen and to overlie an aortic dissecting aneurysm, and in a by-pass graft or a native vessel. Intraluminal endovascular prosthetic grafting is an alternative to conventional vascular surgery. Intraluminal endovascular grafting involves the percutaneous insertion into a blood vessel of a tubular prosthetic graft and its delivery via a catheter to the desired location within the vascular system. The alternative approach to percutaneous revascularization is the surgical placement of vein, artery, or other by-pass segments from the aorta onto the coronary artery, requiring open heart surgery, and significant morbidity and mortality. Advantages of the percutaneous revascularization method over conventional vascular surgery include obviating the need for surgically exposing, incising, removing, replacing, or by-passing the defective blood vessel, including heart—lung by-pass, opening the chest, and general anesthesia.

Revascularization via a prosthetic graft device is desirable in various situations to expand a constricted vessel or to maintain an open passageway through a vessel. A stent may be used to expand a vascular channel or to maintain the expanded lumen, after angioplasty of a coronary artery. In these situations, stents are useful to prevent restenosis of the dilated vessel, to prevent elastic recoil of the vessel, or to eliminate the danger of occlusion caused by "flaps" resulting from intimal tears associated with angioplasty. Stents may be utilized after atherectomy which is the cutting out of plaque to remove it. In such removal of atherosclerotic plaque from the coronary vessel wall, a stent is used to maintain patency of the vessel. Stents are used in by-pass grafts as well, to maintain patency. Stents can also be used to reinforce collapsing structures in the respiratory, biliary, urological, and other tracts.

Existing technology for percutaneous treatment of coronary artery disease either uses balloons or other devices to break open coronary plaque. An angioplasty balloon is inflated within the stenosed vessel, or body passageway, in order to shear and disrupt the wall components of the vessel to obtain an enlarged lumen. This procedure leaves an irregular surface and exposes thrombogenic areas. Clot occurs in some patients, occasionally causing abrupt closure of the coronary artery or vein by-pass segment; in a major portion of angioplastied sites, plaque recurs (restenosis). Thus, although the body passageway may initially be successfully expanded by a balloon dilation procedure, subsequent, early restenosis can occur due to the recoil of the body passageway wall as well as intimal growth which decreases the size of the previously expanded lumen of the body passageway.

Stents, which, prop open vessels, preventing recoil and treating dissections caused by angioplasty have been recently approved for clinical use in the United States. Structures which have previously been used as stents or intraluminal vascular grafts have included coil stainless steel springs; helically wound coil springs manufactured from an expandable heat-sensitive material; and expanding stainless steel stents formed of stainless steel wire in a zigzag or other pattern. These stents are highly thrombogenic and require vigorous anticoagulation, with significant, and occasionally life threatening side effects. Important obstacles encountered after stent placement include coagulation (clot) formation on surfaces of the stent, inflammation around the stent, and undue proliferation of neointima. Because these problems persist, as described in the New England Journal of Medicine (Vol. 331, pages 489–501 and 539–541, 1994), procedures are performed using post-stent treatments, such as anticoagulation drugs. Such drugs are costly and their use may lead to complications, such as uncontrolled hemorrhage, bleeding, and vascular complications. A number of attempts have been made to make stents more compatible with the patient's coagulation system. Foreign materials whether bare metal, polymers, or other materials attract thrombin and platelets as well as other blood constituents that promote the problems described immediately above. Attempts have been made to alter the surface charge, to apply a polymer coating on the stent and to impregnate polymer coatings with drugs such as heparin to enhance tissue and body acceptability, but these approaches themselves have certain deficiencies. Although vascular stents are used in humans, and for experimental purposes in animals, it is desirable to overcome their deficiencies.

Therefore, what is needed is a new design for graft prosthesis, a method for preparing it, and a method for inserting it which avoids complications due to coagulation, restenosis, recoil, inflammation, and other problems.

SUMMARY OF THE INVENTION

In accordance with the present invention, a novel composite prosthesis comprises a tubular structure, typically a blood vessel, and a cylindrical-shaped member. The blood vessel is preferably a vein segment removed from a patient and the cylindrical-shaped member, preferably an expandable stent, is glued, sutured, or in some other fashion affixed to the vein. The vein segment of the combination is referred to as a vein graft or vein implant to distinguish it from the vascular structure into which it is inserted as a part of the combination. This composite prosthesis is then introduced inside a body passageway, such as diseased arterial segment or inside a saphenous vein graft segment which by-passes an arterial segment. It may be introduced by placement over a balloon catheter. When the balloon is inflated the stent and vein graft expand. The stent prevents recoil and keeps the vein graft tissue in place, while the vein graft forms a new inner lining for the vessel. It is preferred that the vein graft portion of the composite prosthesis be the patient's own vein. As an alternative source of tissue, blood vessel segments harvested from other people, including cadavers, or mammals could be used, and are available commercially, and are occasionally used by coronary by-pass surgeons in lieu of the patient's own veins.

It is preferred that the cylindrical-shaped member be an intraluminal vascular graft, or prosthesis, which generally comprise a tubular member having first and second ends and a wall surface disposed between the first and second ends.

Various designs of tubular members are useable as a part of the composite prosthesis. Some have variable initial diameters which determine what the final diameter will be after placement in a body passageway. Others have variable initial and final diameters. Some are held in a contracted state for insertion and then permitted to expand after placement. Still others are expanded by application of force after placement. The invention is not limited to any particular design of tubular member.

The invention is described based on a preferred design but is not limited thereby. Tubular member preferably has a first diameter, d, which permits intraluminal delivery of the tubular member into a body passageway having a lumen. The tubular member preferably has a second diameter, d', which second diameter d' is preferably greater than the first diameter. The second diameter is selected to cause the cylindrical-shaped member to contract or expand the lumen of the body passageway. It is often preferred that the tubular member have a diameter greater than that of the native vessel into which the graft assembly is inserted.

The blood vessel carried by the cylindrical-shaped member is co-extensive with the longitudinal passageway of the cylindrical-shaped member. The blood vessel, preferably a vein, has a radial extent corresponding to the radial extent of the peripheral wall of the cylindrical-shaped member when such member is in an expanded condition or final condition after insertion. It is desired that the blood vessel have a diameter corresponding to the radial extent of the lumen of the body passageway into which the composite graft assembly is being inserted. It is often preferred that the blood vessel have a diameter greater than that of the native vessel.

The vein graft is secured by glue, sutures, or otherwise affixed to the cylindrical-shaped expandable member. The affixing may occur by gluing the stent and vein graft together or by stitching the vein graft to a structural member of the cylindrical-shaped member. Some combination of fixing means such as gluing, welding, and stitching may be used. It is preferred that the vein graft segment be longer than the longitudinal dimension of the cylindrical-shaped member so that excess vein graft protrudes from one or both ends of the cylindrical-shaped member. It could then be folded over the outer surface of the peripheral wall of the cylindrical-shaped member. This forms a sleeve over the outer surface of the wall. The one or more sleeves may be continuous with the entire outer surface. A sleeve at each end of the cylindrical-shaped member is formed to encompass the leading edges of the cylindrical-shaped member and a portion of the outer wall at the respective ends. In one embodiment, the vein graft may be about twice as long as the cylindrical-shaped member and folded. A part of the length of the stent forms an internal lining for the cylindrical-shaped member and another part of the vein forms an outer lining for the cylindrical-shaped member. In such arrangements, the vein graft encompasses the internal surface of the cylindrical-shaped member and at least its end edges as well, so that once the combination is in place in a vascular structure, the cylindrical-shaped member will not be exposed to body fluids in the body passageway.

Accordingly, one object of this invention is to provide a new composite graft prosthesis which prosthesis exposes body fluids and/or body tissue to the more bio-compatible vein graft of the combination prosthesis. Another object is to provide a method for forming the new composite graft prosthesis and a procedure for its insertion and use.

These and other objects, features, and advantages will become apparent from the following description of the preferred embodiments, claims, and accompanying drawings.

BRIEF DESCRIPTION OF THE DRAWINGS

FIG. 1 is an expanded view of a prosthesis 20, catheter 41, and sleeve 40.

FIG. 2 is a perspective view of one embodiment of a cylindrical-shaped member 22 which forms a part of the prosthesis 20.

FIG. 3 is an end view of FIG. 2.

FIG. 4 is a side view of a prosthesis 20 comprising a cylindrical-shaped member 22, and vein graft 26 engaged around a balloon catheter 72. Vein 26 forms sleeves 36, 37 at respective ends of cylindrical-shaped member 22.

FIG. 5 is a side view similar to FIG. 4 but with partial cut away and in an expanded condition, with vein 26 forming a continuous lining over the inside of the cylindrical-shaped member 22 and forming a continuous cover over the external surface of cylindrical-shaped member 22.

FIGS. 10 through 18 are illustrations of various designs of stents usable as the cylindrical-shaped member of the prosthesis of the invention.

In FIG. 20, the vein graft 26 is as long as the cylindrical-shaped member 22.

DETAILED DESCRIPTION OF THE PREFERRED EMBODIMENTS

Figure 6:
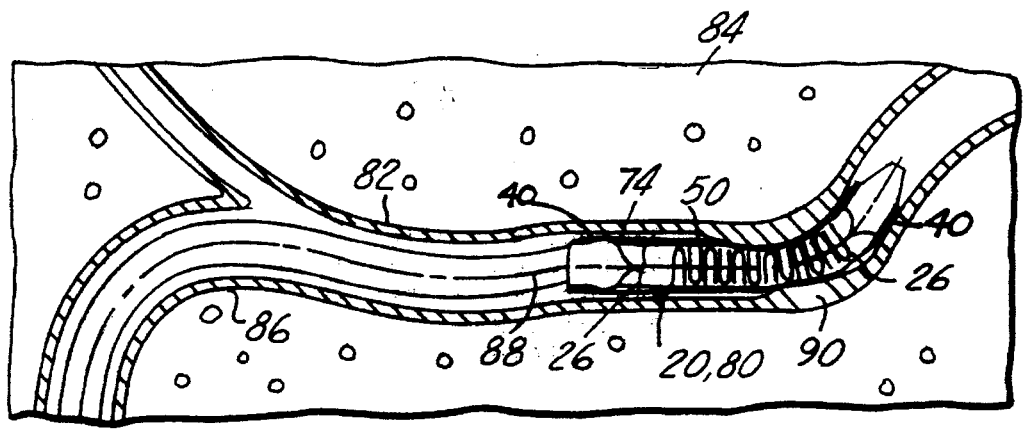
FIG. 6 is a cut away view of a body cavity with the prosthesis 20 of the invention being inserted as a part of a stent/catheter assembly 80.

A preferred expandable intraluminal composite graft assembly, or composite prosthesis, 20 for a body passageway is illustrated in FIG. 1. It comprises a cylindrical-shaped member 22 with a longitudinal passageway 24 and a vein 26 carried in the longitudinal passageway 24 of the cylindrical-shaped member 22. The vein 26 carried by the cylindrical-shaped member 22 is co-extensive with or at least as long as the longitudinal passageway 24 of the cylindrical-shaped member 22. The vein 26 has a radial extent corresponding to the radial extent of the peripheral wall 28 of the cylindrical-shaped member 22 when such member 22 is in an expanded condition. It is preferred that the vein 26 have a diameter corresponding to the radial extent of the lumen of the body passageway into which the composite graft assembly is being inserted. Those skilled in the art will understand that in the case of vascular structures which are partially occluded, the lumen is reduced to the extent of the occlusion. Therefore, a preferred diameter of the vein graft 26 is at least equivalent to the diameter of a reference lumen in a non-occluded condition in the body passageway. For example, it is preferred that the diameter of the graft vein 26 be selected to meet or exceed the referenced diameter of the vessel into which it is being inserted to form a new inner lining. The vein graft 26 is secured by glue or weld 31, sutures 32, or otherwise affixed to the inside surface 30 of the cylindrical-shaped expandable member 22. Some combination of fixing means such as gluing, welding, and stitching may be used, as shown in FIG. 1. It is preferred that the vein graft 26 segment be longer than the longitudinal dimension of the cylindrical-shaped member 22. (See FIGS. 1, 4, 5, 19 and 20.) In this preferred arrangement, excess vein graft 26 protrudes from either end 34, 35 of the cylindrical-shaped member 22. In one alternative, graft 26 protrudes just slightly from either end 34, 35 of member 22. In another alternative, graft 26 is as long as member 22 but does not protrude. In still another alternative, graft 26 protrudes from ends 34, 35 in an amount sufficient to be folded over at least a portion of the outer surface of the peripheral wall 28 of the cylindrical-shaped member 22. This forms a sleeve 36, 37 over the outer surface 38 of wall 28 at respective ends 34, 35. (FIG. 4.) In this arrangement, the vein graft 26 encompasses the internal surface 30 of the cylindrical-shaped member 22 and its end edges 34, 35 as well, so that once the combination is in place in a vascular structure, the cylindrical-shaped member 22 will not be exposed to body fluids in the body passageway. Sleeves 36, 37 may extend along the entire extent of the outer surface 38 to cover the entire outer surface 38. Sleeves 36, 37 may also overlap.

In another embodiment, the vein graft 26 is at least twice as long as the member 22, and the vein graft 26 is inserted into the body passageway 24 of the one end 34 of member 22 and then folded over the other end 35. In this configuration, the vein 26 forms a layer on the inner and outer surfaces of the member 22. The edges 39a, 39b of the vein 26 are then fixed together, by stitches or other means. (FIG. 5.) Other alternative arrangements are described below with respect to FIGS. 19 and 20. In all arrangements, the vein graft 26 forms an inside cover or lining for the member 22.

FIG. 1 shows a composite 20 where the graft vein 26 is held in place within the longitudinal passageway 24 of the cylindrical-shaped member 22 by joints 31 between the cylindrical-shaped member 22 and the graft vein 26 and also by stitches 32 (suturing). Joints 31 are preferably formed by glue or weld. Any combination of glue, stitches, both, or other welding means may be used.

It is preferred that the suture material used to secure the vein graft to the cylindrical-shaped member be a monofilament of bio-compatible material. A bio-compatible glue may be used as an adhesive securing means. Such adhesives are known. One example is a silicone rubber compound containing organosilicon polymers which are adhesives serviceable over a broad temperature range (−100° F. to 500° F.), are resistant to degradation, have low water absorption, and in the medical grade, are bio-compatible.

FIG. 1 shows the composite 20 being prepared prior to insertion into a body passageway. A Teflon sleeve 40 is used to cover the outer surface 38 of the cylindrical-shaped member 22. The sleeve 40 facilitates advancement of the composite 20 into a body passageway and prevents distortion of composite 20. Sleeve 40 also prevents abrasion of body passageway by stitches 32 and prevents contact of the body passageway with the joints 31 during the process of insertion. A balloon catheter assembly 41 is used to insert the composite graft assembly 20. Once the composite graft assembly 20 is inserted, the Teflon sleeve 40 is removed, the balloon is inflated, and then the balloon catheter assembly 41 is removed. Teflon sleeve 40 is also referred to as a delivery sheath.

The invention will now be described with reference to different examples of cylindrical-shaped members but it is to be understood that any cylindrical-shaped member useful as a stent, and particularly an expandable stent, may form a part of the composite graft assembly 20. The descriptions below are exemplary.

A variety of stent designs are usable as the cylindrical-shaped member of the invention. The design of the stent is not critical so long as certain features are present. The stent must be capable of achieving a size sufficient to prevent its migration away from the body passageway into which it is inserted. The configuration of the stent must be compatible with the body passageway so as to prevent erosion or rupture by the stent. The stent should achieve a relatively constant, fixed inner diameter and length after placement. Examples of stent designs are metallic, polymeric, hydrogel, and hydrophilic stents, self-expanding stents formed of spring-type (shape-memory) metals, plastically deformable alloy stents suitable for balloon expansion, stents capable of compaction where compaction introduces stresses into the stent material that act to expand the stent after release from sleeve or restraint in the body passageway. Accordingly, there is no limitation as to the type of material from which the cylindrical body may be fabricated. The material must be geometrically stable, have a suitable expansion ratio, retain flexibility even when compressed to a small diameter, be adaptable to structures of different diameters, and able to maintain a residual expansion force, as by its elasticity, to make dislocation unlikely. Materials such as metals, semi-metals, alloys, polymeric resins, plastics, hydrogels, natural, and synthetic composites are a few examples. Stents may be permanent, temporary, retrievable, bio-degradable or bio-absorbable. It is preferred that they not be bio-degradable or bio-absorbable.

Examples of cylindrical-shaped expandable members, their delivery, expansion, and their use are described in U.S. Pat. Nos. 4,733,665 (Palmaz); 4,739,762 (Palmaz); 4,776,337 (Palmaz), Continuation of 4,733,665; 5,102,417 (Palmaz); 4,580,568 (Gianturco); 4,800,882 (Gianturco); 5,041,126 and 5,314,444, each Continuation of 4,800,882; and 5,195,984 (Schatz); 5,133,732, 4,886,062, and 4,969,458 (Wiktor); 5,282,823 (Schwartz); 5,192,297 (Hull); 5,104,404 (Wolff); 5,258,042 (Mehta); 4,922,905 (Strecker); 5,344,426 (Lau); 5,314,472 (Fontaine); 5,234,456 (Silvestrini); 5,282,824 (Gianturco); and 5,342,621 (Eury), each of which is incorporated herein by reference in its entirety.

Referring to FIG. 2, the cylindrical-shaped member is an expandable stent 50 which has a longitudinal axis 52. The stent 50 comprises a plurality of curved sections 54 that are situated generally perpendicular to the axis 52. Adjacent curved sections 54 are joined by bends or cusps 56. A loop 58 is formed at each free end of the wire stent 50 in order to shield the wire end. The curved sections 54 are formed into a circular configuration, as shown in the end view of FIG. 3, so that the stent 50 has a cylindrical opening 60 formed therein.

The curved sections 54 and cusps 56 form a series of alternating clockwise and counter-clockwise loops 62 and 64, respectively, the clockwise direction relative to the axis 52 has been arbitrarily selected and is noted by the heavy arrow 66 in FIG. 2. In the contracted condition of the stent 50, these loops 62 and 64 overlap longitudinally, as demonstrated by the overlap region 70 shown in FIG. 4. Thus, the overlap region 70 gives the appearance that the stent is a continuous circular ring when viewed from an end (FIG. 3), although when viewed as in FIGS. 4 and 5 it is apparent that the cylindrical shape of the stent 50 is discontinuous. The importance of this feature of stent 50 is illustrated by a comparison of FIGS. 4 and 5 and by further description in U.S. Pat. No. 4,800,882.

In FIG. 4, the composite graft assembly 20 having the stent 50 with a vein 26 carried therein is shown secured around a catheter 72, which has an inflatable balloon 74 adhered thereon surrounding a feed orifice 76 in the catheter. The balloon used in this embodiment is a folded balloon in which flaps 78 of the balloon 74 are folded over the catheter 72, as described in Column 3 of U.S. Pat. No. 4,800,882. The folded flaps 78 allow the balloon 74 to inflate to a specific diameter without excessively stretching the balloon material and risking a rupture of the balloon. Sleeve (sheath) 40 encompasses assembly 20 and balloon 74 and is removed after insertion and prior to balloon inflation.

The stent 50 is compressed about the catheter 72 and balloon so that it assumes a contracted outer diameter d, area A and peripheral extent calibrated to allow insertion into a particular body passageway. The vein 26 collapses along with the compressed stent 50, as shown by the folds 27 of vein 26. The clockwise loops 62 and counter-clockwise loops 64 overlap in the region 70, and the spring stiffness of the wire keeps the stent in this position during insertion. The stent 50 and vein 26 remain in tight contact with the catheter 72 even as the assembly is delivered around curves and bends in a body passageway. Teflon sleeve (sheath) 40 as shown in FIG. 1 and 6 is used to hold the assembly together for delivery. Such sleeve 40 is removed after the catheter 72, stent 50, and vein 26 are fully inserted into the body passageway. The balloon 74 is inflated to an outer diameter d', area A' and second peripheral extent calibrated to force the stent 50 into contact with the body passageway inner surface and, at least in some cases, to expand the passageway. As the balloon is inflated, the clockwise and counter-clockwise loops 62 and 64 diverge circumferentially until the longitudinal overlap between loops is reduced to the region 79, shown in FIG. 5. Thus, the effective diameter of the stent 50 relative to the longitudinal axis 52 is increased. This causes the collapsed vein 26 to open and be retained in an open position due to its attachment to the expanded stent 50. It should be noted that the inner diameter (id) of the stent is proportionally changed from id to id' along with the outer diameter changing from d to d', as the thickness of the wire of the stent is essentially unchanged.

In a method of using the composite graft assembly 20 of the present invention, the composite graft assembly 20 and balloon catheter assembly 80 are inserted into a passageway 82, such as an artery, in a patient's body 84, as shown in FIG. 6. The assembly 80 is in the deflated configuration as it is maneuvered around the curve 86 in the body passageway 82. The stiffness of the catheter 88 allows the assembly 80 to follow the curve 86, while the strength and stiffness of the stent 50 keeps it tightly engaged on the catheter balloon 74 during insertion. The passageway has an occlusion 90 situated at another bend in the passageway 82.

Figure 7:
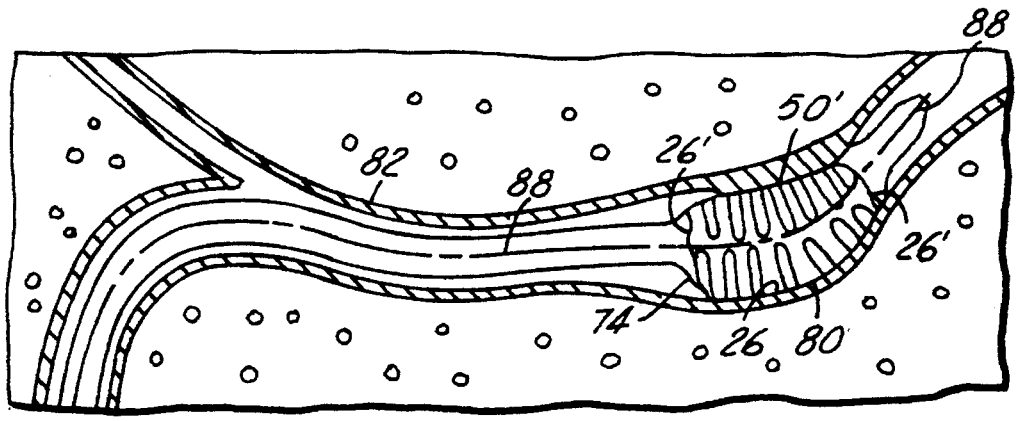
FIG. 7 is a view similar to FIG. 6 with the balloon catheter inflated and with the prosthesis 20 in contact with the body cavity wall.

In FIG. 6, the stent and balloon catheter assembly 80 is shown fully inserted into the passageway 82 so that the stent 50 and balloon 74 are situated directly adjacent the occlusion 90 and following the curve of the body passageway. The assembly is shown in the expanded configuration 80' in FIG. 7, in which the balloon 74' is inflated and the wire stent 50' expanded to contact and enlarge the body passageway 82. The expansion is exaggerated in FIG. 7 for clarity. The balloon catheter assembly 80 and the composite graft assembly are each expanded a sufficient amount to reduce or eliminate the occlusion 90 and open the body passageway 82. The balloon is then deflated and the catheter removed, leaving the stent 50 to hold the body passageway open and to hold the vein graft 26' open, while vein graft 26' provides tissue surface in contact with the fluid of the body passageway 82. By this configuration, the advantage of an open lumen are achieved without thrombogenic difficulties inherent when a foreign substance (i.e., wire stent) contacts blood.

Figure 8:
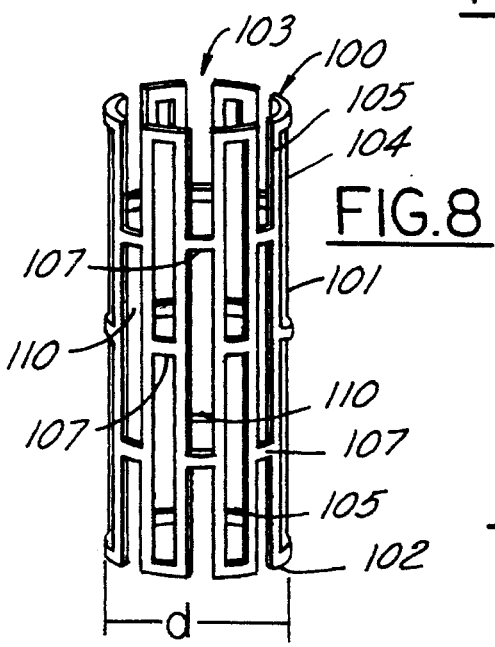
FIG. 8 is a perspective view of another embodiment of an expandable cylindrical-shaped member 22 which forms a part of a prosthesis 20. The cylindrical-shaped member 22 is at a first diameter, d.
Figure 9:
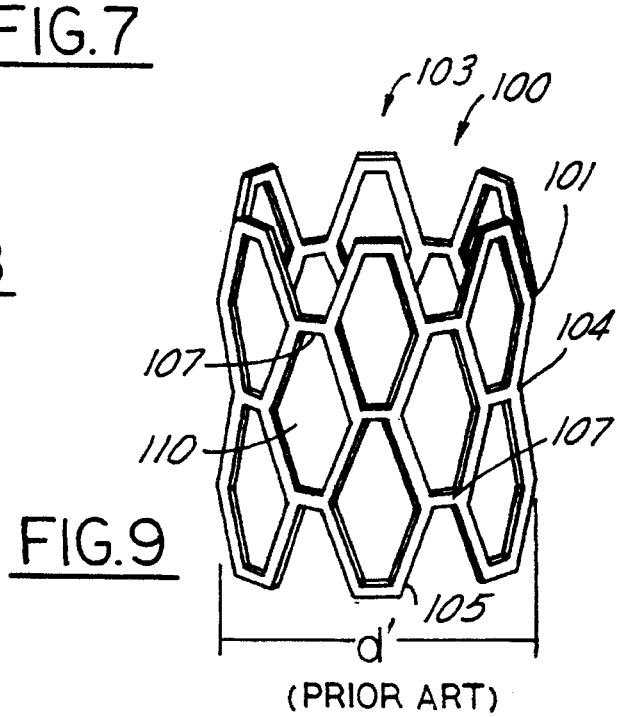
FIG. 9 is a perspective view similar to FIG. 8 but with the cylindrical-shaped member 22 in an expanded condition at a second diameter, d'.

With reference to FIGS. 8 and 9, the cylindrical-shaped member is an expandable intraluminal vascular graft, or prosthesis, 100, which generally comprise a tubular member 101 having first and second ends 102, 103 and a wall surface 104 disposed between the first and second ends 102, 103. Tubular member 101 has a first diameter, d, which permits intraluminal delivery of the tubular member 101 into a body passageway having a lumen. With reference to FIG. 9, upon the application from the interior of the tubular member 101 of a radially, outwardly extending force, tubular member 101 has a second, expanded diameter, d', which second diameter d', is variable in size and dependent upon the amount of force applied to deform the tubular member 101.

Tubular member 101, may be any suitable material which is compatible with the human body and the bodily fluids (not shown) with which the vascular graft, or prosthesis, 100 may come into contact. Tubular member 101 must also be made of a material which has the requisite strength, plastic and elastic characteristics to permit the tubular member 101 to be expanded and/or deformed from the configuration shown in FIG. 8 to the configuration shown in FIG. 9 and further to permit the tubular member 101 to retain its expanded and deformed configuration with the enlarged diameter d' shown in FIG. 9 and resist radial collapse. Suitable materials for the fabrication of tubular member 101 would include silver, tantalum, stainless steel, gold, titanium, or other metal, or any suitable plastic material having the requisite characteristics previously described and as further described for tubular members in U.S. Pat. No. 5,195,984 and in other patents incorporated herein by reference.

It should be noted that not only is tubular member 101 expanded from the configuration shown in FIG. 8 to achieve the configuration shown in FIG. 9, but tubular member 101 is further "deformed" to achieve that configuration. By use of the term "deformed" is meant that the material from which graft, or prosthesis, 100 is manufactured is subjected to a force which is greater than the elastic limit of the material utilized to make tubular member 101. Accordingly, the force is sufficient to permanently or semi-permanently bend elongate members 105 whereby segments of the elongate members 105 pivot about connecting members 107 and move in a circumferential direction as they pivot, whereby the diameter of the tubular member 101 increases from the first diameter, d, to the expanded diameter, d', of FIG. 9 The force to be applied to expand tubular member 102 must be sufficient to not only expand tubular member 101, but also to deform elongate member 105, whereby the portions of the elongate members 105 which pivot about the ends of connecting members 107 do not "spring back" and assume their configuration shown in FIG. 8. Rather, they retain the configuration of FIG. 9 and are rigid in the sense of having an outer shape maintained by a fixed frame work, and not pliant. Tubular member 101, is initially a thin-walled tube having a uniform wall thickness. A plurality of slots or openings 110 formed in the wall surface 104 of tubular member 101. Change configuration from FIG. 8 to FIG. 9. The longitudinal diameter of the slots 110 is reduced and the lateral (radial circumferential) dimension increased. Once graft prosthesis 100 has been expanded and deformed into the configuration shown in FIG. 9, graft prosthesis 100 will serve to prevent a body passageway from collapsing and hold vein 26 in an open position.

Figure 10:
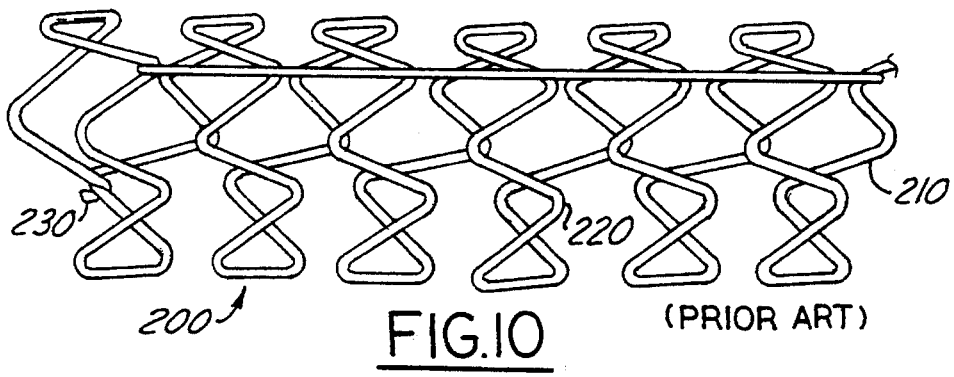
Figure 11:
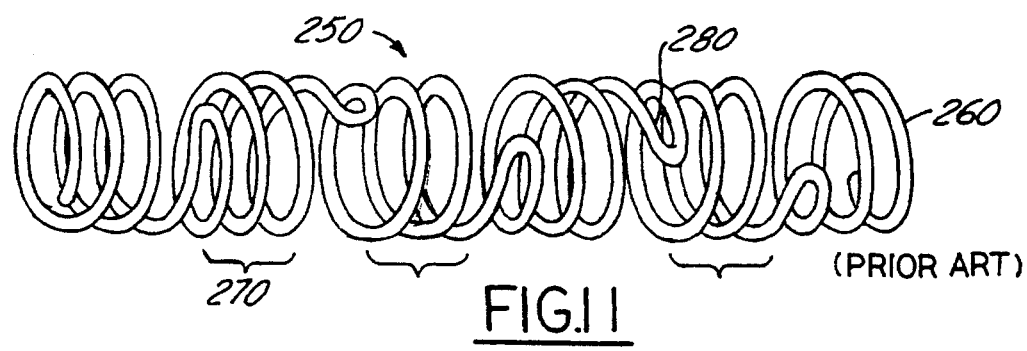
Figure 12:
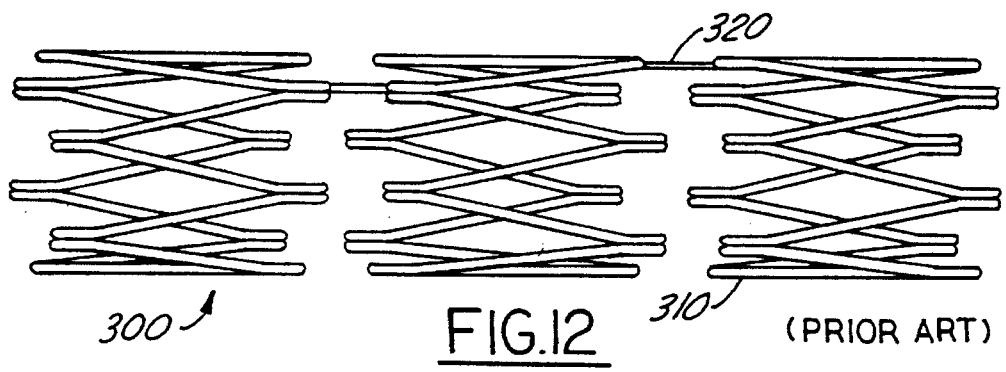
Figure 13:
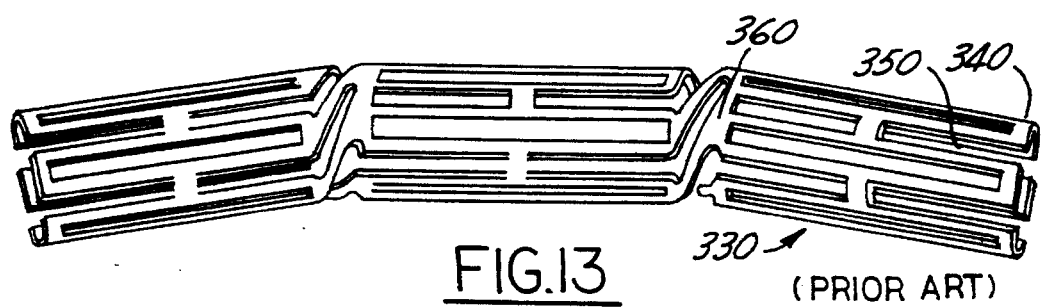
Figure 19:
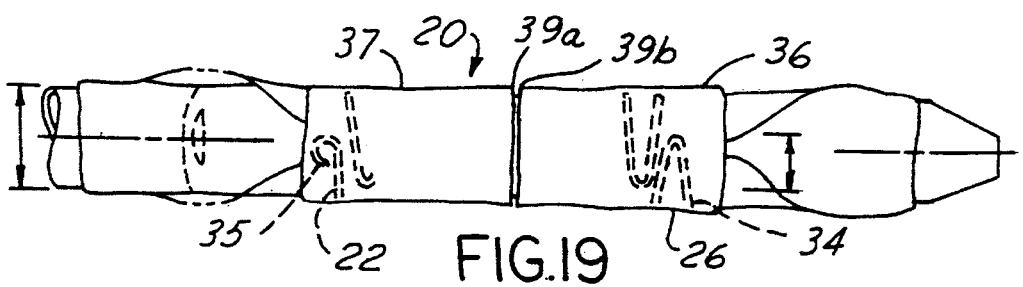
FIG. 19 is a side view similar to FIG. 4 but with the sleeves 36, 37 meeting about in the middle of the cylindrical-shaped member 22.

As per the patents previously incorporated herein by reference, there are a variety of other stent designs. The invention is not limited to any particular design. However, further examples are given below to further facilitate use of the invention. U.S. Pat. Nos. 4,886,062 and 5,133,732 to Wiktor describe a stent 200 with a cylindrical body formed of generally continuous wire 210 having a deformable zigzag 220 wherein the wire is a coil of successive windings and the zigzag is in the form of a sinusoidal waves, whereby the stent body may be expanded from the first unexpanded diameter to a second expanded diameter by the force of an inflating balloon. There are also means such as hooks 230 for preventing the stent body from stretching along its longitudinal axis. (See FIG. 10.) U.S. Pat. No. 4,969,458 to Wiktor shows a stent 250 which is a wire 260 winding in a hollow cylindrical shape. The winding includes a series of groups of helical coils 270 along the length of the winding while providing radial strength. The coils of each group are wound in a direction opposite to the winding of the next adjacent group of coils. A reversely turned loop 280 joining each to successive groups allows for smooth expansion of the adjacent group of coils. (See FIG. 11.) U.S. Pat. No. 5,282,823 to Schwartz shows a stent 300 comprising a cylindrical shaped body which comprises a plurality of substantially helical metal elements 310 joined to allow flexing of the stent along its longitudinal axis. The helical wire winding is substantially continuous and there is a polymeric connector 320 extending between the helical metal elements to provide strain relief means. (See FIG. 12.) U.S. Pat. No. 5,104,404 to Wolff is similar. U.S. Pat. No. 5,102,417 is similar in design to U.S. Pat. No. 5,195,984 described earlier hereinabove and assigned to the same assignee. U.S. Pat. No. 5,102,417 shows a plurality of expandable and deformable vascular grafts 330 which are thin wall tubular members 340 having a plurality of slots 350 disposed substantially parallel to the longitudinal axis of the tubular members and adjacent grafts are flexibly connected by at least one connector member 360. (See FIG. 13.) A deformed and expanded configuration is similar to FIG. 9. U.S. Pat. Nos. 5,102,417; 4,739,762; 4,733,665; and 4,776,337 are all by Palmaz. The Palmaz patents are similar in design to the '417 and the '984 patents described earlier hereinabove. U.S. Pat. No. 4,580,568 to Gianturco describes a stent 400 comprising a wire formed into a closed zigzag configuration including an endless series of straight sections 410 and a plurality of bends 420. The straight sections are joined by the bends to form the stent. (See FIG. 14.) The stent is resiliently depressible into a small first shape wherein the straight sections are arranged side by side and closely adjacent one another for insertion into a passageway and the bends are stored stressed therein. The stent is resiliently expandable by release of the stresses stored in the bends to a second shape which presses the straight sections against the wall of the body passageway. U.S. Pat. No. 5,282,824 to Gianturco describes a stent similar to U.S. Pat. No. 4,580,568 where straight section 410 are joined at bends 420 by joints. U.S. Pat. No. 5,041,126 to Gianturco is similar to U.S. Pat. No. 4,800,882 described hereinabove. U.S. Pat. No. 4,922,905 to Strecker describes a tubular stent 450 with a wall structure defined by loosely interlocked loops 460. (See. FIG. 15.)

The stent has a first relatively small diameter for introduction into a body passageway and the loops are capable of progressive, permanent deformation with attendant radial expansion in response to increasing expansion by a catheter. In its preferred embodiment Strecker's stent is a wire mesh tube of a single tantalum filament of 0.1 millimeters which is knit into a series of loosely woven loops providing longitudinal and radial flexibility for insertion. During balloon expansion the loops are distended by mechanical deformation so that the wire struts move apart and become locked at their intersecting junction sites 480. U.S. Pat. No. 5,314,472 to Fontaine describes a vascular stent 500 having a longitudinal axis comprising a wire bent 510 into a wave form pattern and spirally wrapped into a hollow cylindrical shape around a forming mandril. 520. (See FIG. 16.) U.S. Pat. No. 5,344,426 to Lau describes a stent 550 formed from a sheet material 560 having a open reticulated design including a plurality of apertures 570 with a plurality of finger like projections 580 aligned in rows. The elongated cylindrical structure has some of the finger like projections intersecting some of the apertures in an interlocking relationship. (See FIG. 17.) U.S. Pat. Nos. 5,234,456 to Silvestrini and U.S. Pat. No. 5,258,042 to Mehta describe a stent for placement in a body lumen which has a wall structure at least a portion of which is comprised of a hydrophilic or hydrogel material capable of absorbing body liquid to thereby increase the volume of the material and cause the external diameter of the stent to become engaged with the wall of the body passageway.

Perhaps the simplest stent design is referred to as the Wallstent which is a cylindrical shaped stent 600 formed for a stainless steel alloy with a self-expanding mesh design 610. It is maintained in a constrained and elongated arrangement on a delivery system by a sleeve. Retraction of the sleeve releases the stent 600 which returns to its original position by its self-expanding property. (See FIG. 18.)

Figure 20:
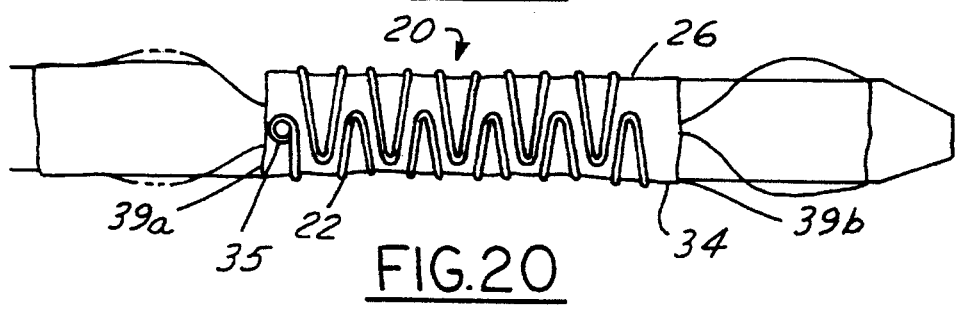
FIG. 20 is a side view similar to FIG. 4 but without sleeves 36, 37.

As described earlier in connection with FIGS. 1 through 5, the composite prosthesis 20 comprises the cylindrical-shaped member 22 and a tubular structure 26, preferable a vessel. The vessel is preferably a vein 26 and desirably at least as long as member 22. It is preferred that the vein 26 protrude from ends 34, 35 of the cylindrical-shaped member 22 as shown FIG. 1. The protruding ends are folded over to form sleeves 36, 37, as in FIG. 4. In another arrangement, as FIG. 5, the vein 26 is about twice as long as the cylindrical-shaped member 22 and forms both an internal lining of the member 22 and an external cover for the member 22. In still another embodiment, as in FIG. 19, the vein 26 forms an internal lining and external cover where the two end edges 39a, 39b of the vein 26 meet about midway between ends 34, 35 of the member 22. The edges 39a, 39b, are secured by a variety of means. They may be fixed together, secured to the cylindrical-shaped member 22 or fixed to an opposite surface of the vein 26 which forms the internal lining of the cylindrical-shaped member 22. Such securing may be by glue, weld or stitching. In still another embodiment, the vein 26 may be as long as the member 22 and not protrude from the ends 34, 35, of member 22 as shown in FIG. 20. In FIG. 20 the end edges 39a, 39b of vein 26 are about even with the ends 34, 35 of the cylindrical-shaped member 22.

Experimental Procedure For Preparation of
Composite Prosthesis Using Rabbit Vein A rabbit was anesthetized with ketamine (35 mg/kg), xylazine (5 mg/kg), and acepromazine (0.75 mg/kg). A neck midline cut down was performed to allow access to both jugular veins. A jugular vein was identified, isolated, and cleaned of associated tissue. A two to three centimeter length of vessel was ligated at both ends, cut, and removed to a room temperature bath of physiological salt solution. A jugular vein segment was removed from the bath, and under dissection microscope, sutured to a stent as per the configuration shown in FIGS. 1, 2, and 4.

Experimental Implant Protocol for Rabbit

Rabbits are anesthetized as described above and a vein stent assembly arrangement is prepared using the jugular vein segment as described above. In addition, the companion carotid artery is isolated and a catheter sheath inserted. This procedure is repeated on the contralateral jugular and carotid vessels. While the carotids are being prepared, the vein stent segment is assembled as described above. The catheter with the vein/stent wrapped over a deflated balloon is slipped into a Teflon sleeve to cover the entire catheter length, and the assembly as shown in FIG. 1 inserted through the carotid artery sheath. The catheter is fed into the iliac artery under fluoroscopic guidance, the Teflon sleeve pulled back, and the balloon inflated for one minute to deploy the stent. This maneuver positions the jugular vein segment inside the iliac artery. The Teflon sleeve and balloon catheter are removed from the vascular system, fitted with the second jugular vein segment and stent, and the procedure is repeated for the contralateral iliac artery. The Teflon sleeve and catheter are removed and replaced by an open lumen catheter. Radiopaque dye is injected through the open lumen catheter with tip position just above the bifurcation of the iliac arteries, and the patency of the vein segment with an each iliac artery is evaluated under fluoroscopy. A segment of each iliac with the vein graft is removed and examined to determine the presence or absence of thrombus on the endothelial surface and the maintenance of the diameter of the iliac lumen equivalent to the diameter at the time of an initial insertion and expansion.

Procedure for Implant of Composite Prosthesis

Utilizing standard procedures for balloon angioplasty, stents are placed at the site of a vascular lesion or occlusion and expanded at the site for placement, to expand a body passageway to its usual expanded dimension, or to hold such body passageway open. A general description of a procedure for inserting a conventional stent can be found in U.S. Pat. No. 4,580,568 incorporated herein by reference in its entirety. Manufacturers of stents, such as Johnson & Johnson provide directions for insertion of conventional stents and for post-stent treatment for complications such as anticoagulation and monitoring of same. The procedure for installing the stent of the invention differs from conventional procedures in its use of the patient's own blood vessel, preferably a vein, as an internal lining for a composite graft assembly. The method of the invention will be illustrated by use of a vein to form a composite for insertion into an arterial segment. The invention is not limited thereby. Any one of the body's tubular structures, preferably a blood vessel, is used to repair another of the body's tubular structures, such as a vein, in a saphenous vein by-pass graft, or an artery. In one example of the method of the invention, a vein from the patient is taken from a non-essential portion of the vascular system, such as the saphenous vein of the leg or brachial vein of the arm. The harvested vein from, for example, a cadaver or an animal such as a pig may also be used. In a preferred method the vein which forms part of the composite is an internal saphenous vein of the leg taken from the patient. This extracted vein, referred to as vein graft, is inserted into the cylindrical-shaped member or stent and secured thereto by glue, suturing, or other means. Utilizing standard procedures for balloon angioplasty, an introducer or guiding catheter is placed in the ostium of the artery having the lesion or occlusion to be treated. Under fluoroscopic monitoring, the occluded area is gently probed with a vascular guide wire. Once the lesion is traversed, a standard balloon angioplasty procedure is conducted. Following a wire exchange, if necessary, the balloon angioplasty catheter is withdrawn leaving the guide wire positioned across the lesion or occlusion. The position of the sheath over the stent is verified. Next, it is preferred that saline be injected through the sheath to purge the system and to facilitate sheath withdrawal. Then, the sheathed composite graft assembly of the invention along with the balloon catheter assembly is advanced over the exchange wire to the site of the previously dilated lesion or occlusion. Under fluoroscopic monitoring, the sheath is pulled back exposing the stent at the lesion site. Radiopaque markers of the balloon catheter bracket the dilated lesion to assure positioning of the stent where desired. An inflation device is attached to the balloon catheter assembly to inflate the balloon to the desire pressure. The pressure of inflation will correspond to that pressure recommended by the manufacturer based upon balloon diameter and nominal length and nominal diameter of the stent. The typical inflation pressure is 5 atmospheres. Balloon diameters typically range from 3 to 4 mm, stent length at nominal diameter, in the case of the illustrated stent of FIG. 2 is 15.1 mm to 14.3 mm with the maximum recommended inflation pressure ranging from 8 to 6 atmospheres. However, length may be any length, e.g., 80 mm, and any diameter may be used, e.g., 2 mm to 6 mm. It is typical to exceed the referenced diameter of the arterial segment by 0.25 mm to 1.0 mm and often by 0.5 mm. Stent expansion is monitored in order to achieve the optimum expanded stent diameter as compared to the proximal and distal native artery diameters (reference vessel diameter). When optimally expanded, the stent will be in full contact with the vascular wall and the final stent internal diameter approximately matches the size of the reference vessel diameter. To complete the procedure, the delivery catheter assembly, sheath, and guiding catheter are removed through the sheath introducer.

In conventional post-stent insertion procedure, it is necessary to continue to treat the patient with dextran, aspirin, dipyridamole, heparin and/or Coumadin until the partial thromboplastin time (PTT), the prothrobin time (PT), and internal normalization ratios (INR) reach acceptable or target levels. Complications frequently arise. In contrast, the prosthesis of the invention allows development of a stent to provide desired open lumen while avoiding complex post-stent treatment due to foreign body reaction. This advantage is achieved because the composite prosthesis of the invention comprises a healthy body tissue lining, avoiding exposure of the stent, itself, to circulating body fluids. Such body tissue lining could be patient's own recently extracted blood vessel or a thawed vessel which had been previously harvested and frozen.

While this invention has been described in terms of certain embodiments thereof, it is not intended that it be limited to the above description, but rather only to the extent set forth in the following claims.

The embodiments of the invention in which an exclusive property or privilege is claimed are defined in the following claims.

What is claimed is:

1. An assembly for insertion into a body passageway comprising:
   a. a cylindrical-shaped member having first and second ends, a longitudinal axis between said ends, one or more structural members between said ends defining a peripheral wall, and a longitudinal passage along said longitudinal axis between said ends, said cylindrical-shaped member having a first diameter which permits intraluminal delivery of said cylindrical-shaped member into a body passageway having a lumen, and second diameter greater than said first diameter, whereby said cylindrical-shaped member is expandable to contact or to expand the lumen of the body passageway;
   b. a blood vessel within said longitudinal passage of said cylindrical-shaped member, said blood vessel being at least as long as said axial extent of said longitudinal passage and having a radial extent corresponding to the radial extent of said peripheral wall when said cylindrical-shaped member is in an expanded condition; and
   c. securing means for securing said blood vessel within said cylindrical-shaped member to cause said blood vessel to move with said cylindrical-shaped member to and from said first diameter and said second diameter.

2. The assembly according to claim 1 wherein said blood vessel has a length longer than said longitudinal passage of said cylindrical-shaped member and said blood vessel extends beyond at least one of said first and second ends of said cylindrical-shaped member.

3. The assembly according to claim 2 wherein said blood vessel is folded over a respective edge of said end and overlies at least a portion of the external surface of said peripheral wall of said end.

4. An assembly for insertion into a body passageway comprising:
   a. a cylindrical-shaped member having first and second ends, a longitudinal axis between said ends, one or more structural members between said ends defining a peripheral wall, and a longitudinal passage along said longitudinal axis between said ends, said cylindrical-shaped member having a first diameter which permits intraluminal delivery of said cylindrical-shaped member into a body passageway having a lumen, and second diameter greater than said first diameter, whereby said cylindrical-shaped member is expandable to contact or to expand the lumen of the body passageway;
   b. a blood vessel within said longitudinal passage of said cylindrical-shaped member, said blood vessel having a length longer than said longitudinal passage and having a radial extent corresponding to the radial extent of said peripheral wall when said cylindrical-shaped member is in an expanded condition, wherein said blood vessel extends beyond both of said ends and is folded over respective edges at both of said ends; and
   c. securing means for securing said blood vessel within said cylindrical-shaped member to cause said blood vessel to move with said cylindrical-shaped member to and from said first diameter and said second diameter.

5. The assembly according to claim 1 or 4 wherein said structural member is in the form of a wire formed into a serpentine configuration including a plurality of loops with cusps of adjacent loops in opposing orientation forming an overlap region which adjusts to provide said first and second diameters.

6. The assembly according to claim 1 or 4 wherein said cylindrical-shaped member is a thin walled tubular member, and said one or more structural members define openings in the form of slots being disposed substantially parallel to the longitudinal axis of the tubular member, said slots being deformable to a fixed shape forming a fixed framework to support said blood vessel.

7. The assembly according to claim 1 or 4 wherein said one or more structural members have a substantially uniform thickness which is maintained during adjustment between first and second positions defining said first and second diameters which are outer diameters of said cylindrical-shaped member.

8. The assembly according to claim 1 or 4 wherein said securing means comprises glue.

9. The assembly according to claim 1 or 4 wherein said securing means comprises welds.

10. The assembly according to claim 1 or 4 wherein said securing means comprises stitches.

11. An assembly for insertion into a body passageway comprising:
    a. a cylindrical-shaped member having first and second ends, longitudinal axis between said ends, one or more structurally members between said ends defining a peripheral wall, and longitudinal passage along said longitudinal axis between said ends, said cylindrical-shaped member having a first diameter which permits intraluminal delivery of said cylindrical-shaped member into a body passageway having a lumen, and second diameter greater than said first diameter, whereby said cylindrical-shaped member is expandable to contact or to expand the lumen of the body passageway;
    b. a blood vessel within said longitudinal passage of said cylindrical-shaped member, said blood vessel having a length longer than said axial extent of said longitudinal passage and having a radial extent corresponding to the radial extent of said peripheral wall when said cylindrical-shaped member is in an expanded condition, and wherein said blood vessel extends beyond at least one of said first and second ends of said cylindrical-shaped member, said blood vessel is folded over a respective edge of said end and overlies at portion of the external surface of said peripheral wall of said end, and wherein said blood vessel encompasses the entire external surface of said cylindrical-shaped member; and
    c. securing means for securing said blood vessel within said cylindrical-shaped member to cause said blood vessel to move with said cylindrical-shaped member to and from said first diameter and said second diameter.

12. An assembly for insertion into a body passageway comprising:
    a. a cylindrical-shaped member having first and second ends, a longitudinal axis between said ends, one or more structural members between said ends defining a peripheral wall, and a longitudinal passage along said longitudinal axis between said ends, said cylindrical-shaped member having a first diameter which permits intraluminal delivery of said cylindrical-shaped member into a body passageway having a lumen, and second diameter greater than said first diameter, whereby said cylindrical-shaped member is expandable to contact or to expand the lumen of the body passageway;
    b. a blood vessel within said longitudinal passage of said cylindrical-shaped member, said blood vessel being at least as long as said axial extent of said longitudinal passage and having a radial extent corresponding to the radial extent of said peripheral wall when said cylindrical-shaped member is in an expanded condition;

c. securing means for securing said blood vessel within said cylindrical-shaped member to cause said blood vessel to move with said cylindrical-shaped member to and from said first diameter and said second diameter; and d. a delivery sheath which encompasses said cylindrical-shaped member and said blood vessel.

13. A assembly for insertion into a body passageway comprising:

a. a cylindrical-shaped member having first and second ends, longitudinal axis between said ends, one or more structural members between said ends defining a peripheral wall, and a longitudinal passage along said longitudinal axis between said ends, said cylindrical-shaped member having a first diameter which permits intraluminal delivery of said cylindrical-shaped member into a body passageway having a lumen, and second diameter greater than said first diameter, whereby said cylindrical-shaped member is expandable to contact or to expand the lumen of the body passageway;

b. a blood vessel within said longitudinal passage of said cylindrical-shaped member, said blood vessel being at least as long as said axial extent of said longitudinal passage and having a radial extent corresponding to the radial extent of said peripheral wall when said cylindrical-shaped member is in an expanded condition;

c. securing means for securing said blood vessel within said cylindrical-shaped member to cause said blood vessel to move with said cylindrical-shaped member to and from said first diameter and said second diameter; and d. expansion means within said cylindrical-shaped member for radially expanding said cylindrical-shaped member within a body passageway.

14. The assembly according to claim 13 wherein said means for radially expanding is a balloon catheter, said balloon catheter being received within said longitudinal passage and extending along said longitudinal axis, whereby as said balloon catheter is inflated, said balloon contacts said blood vessel and said cylindrical-shaped member to radially expand said blood vessel and said cylindrical-shaped member.

15. An assembly for insertion into a body passageway comprising:

a. a cylindrical-shaped member having first and second ends, a longitudinal axis between said ends, one or more structural members between said ends defining a peripheral wall, and a longitudinal passage along said longitudinal axis between said ends, said cylindrical-shaped member having a first diameter which permits intraluminal delivery of said cylindrical-shaped member into a body passageway having a lumen, and second diameter greater than said first diameter, whereby said cylindrical-shaped member is expandable to contact or to expand the lumen of the body passageway and wherein said one or more structural members are adjustable to said second diameter by deformation, by stress relief, by hinges between said structural members, or by increasing the thickness of said structural members;

b. a blood vessel within said longitudinal passage of said cylindrical-shaped member, said blood vessel being at least as long as said axial extent of said longitudinal passage and having a radial extent corresponding to the radial extent of said peripheral wall when said cylindrical shaped member is in an expanded condition; and c. securing means for securing said blood vessel within said cylindrical-shaped member to cause said blood vessel to move with said cylindrical-shaped member to and from said first diameter and said second diameter.

16. The assembly according to claim 1, 3, 4, 11, 12, 13, or 15 wherein said blood vessel is a vein.

17. The assembly according to claim 1, 3, 12, 13, or 15 wherein said blood vessel has a length about as long as said longitudinal passage of said cylindrical-shaped member.

18. A method for implanting a composite graft within a body passageway comprising:

a. providing a composite prosthesis comprising an expandable member comprising a cylindrical-shaped member having first and second ends, a longitudinal axis between said ends, one or more structural members between said ends defining a peripheral wall, and a longitudinal passage along said longitudinal axis between said ends; and a blood vessel carried by said cylindrical-shaped member within said longitudinal passage, said blood vessel being at least as long as said axial extent of said longitudinal passage and having a radial extent corresponding to the radial extent of said peripheral wall when said cylindrical-shaped member is in an expanded condition;

b. disposing said prosthesis on a catheter;

c. inserting said prosthesis and catheter within a body passageway by catheterization of the body passageway; and d. expanding said prothesis to bring said prosthesis into contact with the body passageway and to implant said prosthesis in the passageway.

19. The method according to claim 18 wherein the expanding of said prosthesis causes enlargement of the lumen of the body passageway.

20. A method for forming a composite graft comprising:

a. providing an expandable member comprising a cylindrical-shaped member having first and second ends, a longitudinal axis between said ends, one or more structural members between said ends defining a peripheral wall, and a longitudinal passage along said longitudinal axis between said ends;

b. providing a blood vessel having a length greater than the axial extent of said passage of said cylindrical-shaped member;

c. positioning the blood vessel within said longitudinal passage of said cylindrical-shaped member so that a portion of said blood vessel protrudes from at least one of said ends;

d. folding said protruding portion of said blood vessel over the edge of said end and over at least a portion of the external surface of said peripheral wall; and e. securing said blood vessel to said cylindrical-shaped member.

21. The method according to claim 20 wherein step (c) is conducted so that the blood vessel protrudes from both of said ends and step (d) is conducted at both of said ends.

* * * * *